United States Patent [19]

Nay et al.

[11] Patent Number: 5,585,316

[45] Date of Patent: Dec. 17, 1996

[54] CATALYST TREATMENT

[75] Inventors: Barry Nay, Woking; Mark R. Smith, Sunbury-on-Thames; Clive D. Telford, Sunninghill, all of England

[73] Assignee: British Petroleum Company p.l.c.

[21] Appl. No.: 245,067

[22] Filed: May 17, 1994

Related U.S. Application Data

[63] Continuation of Ser. No. 907,889, Jul. 2, 1992, abandoned.

[30] Foreign Application Priority Data

Jul. 2, 1991 [GB] United Kingdom .................. 9114314

[51] Int. Cl.⁶ .............................. B01J 20/30; B01J 38/18
[52] U.S. Cl. ................................ 502/50; 502/34; 502/38; 502/53; 502/329; 502/325
[58] Field of Search ........................ 502/34, 50, 53, 502/325, 329, 38

[56] References Cited

U.S. PATENT DOCUMENTS

| | | | |
|---|---|---|---|
| 2,582,713 | 1/1952 | Martin et al. | 502/50 |
| 2,771,481 | 11/1956 | Rottig et al. | 502/34 |
| 4,039,302 | 8/1977 | Khera | 502/307 |
| 4,826,800 | 5/1989 | McAteer | 502/329 |

FOREIGN PATENT DOCUMENTS

| | | |
|---|---|---|
| 110357 | 11/1983 | European Pat. Off. . |
| 142888 | 11/1984 | European Pat. Off. . |
| 142887 | 11/1984 | European Pat. Off. . |
| 153780 | 2/1985 | European Pat. Off. . |
| 153781 | 2/1985 | European Pat. Off. . |
| 281698 | 3/1987 | European Pat. Off. . |
| 1011967 | 5/1949 | France . |
| 1108326 | 9/1954 | France . |
| 977498 | 7/1949 | Germany . |
| 206335 | 11/1982 | New Zealand . |
| 210549 | 12/1983 | New Zealand . |
| 212820 | 7/1984 | New Zealand . |
| 213328 | 2/1985 | New Zealand . |
| 692234 | 4/1951 | United Kingdom . |
| 2153250 | 1/1985 | United Kingdom . |
| 90/07377 | 12/1989 | WIPO . |

OTHER PUBLICATIONS

"Hydrogenation of CO and $CO_2$ Over Iron Foils Correlations of Rate, Product Distribution, and Surface Composition", Journal of Catalysis 52, 291–301, (1978).

"A Mossbauer Investigation of Iron–Containing Catalysts Prepared at Low Temperatures and Active for Carbon Monoxide Hydrogenation", F. J. Benny et al., *J. Chem. Soc.*, 1989, 85(2), 467–477.

"The Performance of Iron–Containing Catalysts Prepared at Low Temperature for Carbon Monoxide Hydrogenation", Hyperfine Interactions 67, (1991) 549–558.

*Primary Examiner*—Asok Pal
*Assistant Examiner*—Bekir L. Yildirim
*Attorney, Agent, or Firm*—Fay, Sharpe, Beall, Fagan, Minnich & McKee

[57] ABSTRACT

A cobalt catalyst for use in the Fischer Tropsch reaction of synthesis gas to form hydrocarbons is activated or regenerated by treatment of a cobalt containing catalyst with a gas containing carbon monoxide, said gas containing less than 30% v hydrogen. The catalyst obtained has increased activity and greater selectivity towards producing $C_{5+}$ hydrocarbons.

17 Claims, No Drawings

CATALYST TREATMENT

This is a continuation of application Ser. No. 907,889, filed Jul. 2, 1992 abandoned.

This invention relates to a catalyst treatment for a Fischer-Tropsch process.

The Fischer-Tropsch process for the conversion of synthesis gas into hydrocarbons over an iron or cobalt containing catalyst is very well known. Various different methods of either activating a fresh catalyst or regenerating a used catalyst have been proposed. Most preferred is the treatment of the catalyst with hydrogen especially alone, but the use of hydrogen mixed with a minor proportion of carbon monoxide has also been described (see e.g. U.S. Pat. No. 4,626,552). DE 977498 describes the pretreatment with a carbon monoxide containing gas of a catalyst of Group VIII of the Periodic Table, especially an iron one, for the hydrogenation of carbon monoxide.

We have now found a special treatment programme for cobalt-containing catalysts which can be incorporated into a Fischer-Tropsch reaction to increase the catalyst activity and/or increase the selectivity for producing $C_{5+}$ hydrocarbons.

Accordingly the present invention provides a treatment process for a cobalt-containing catalyst which comprises treating the catalyst at elevated temperature with a gas containing carbon monoxide, said gas containing less than 30% v of hydrogen.

The elevated temperature is usually in the range of from 100° to 500° C., preferably 200° to 350° C. and in particular at a temperature above the mean temperature in the subsequent Fischer Tropsch process preferably at least 10° C. above said temperature such as 10°–60° C. or especially 25°–55° C. above; most preferred elevated temperatures are 220°–260° C. especially around 250° C.

The gas used may be composed substantially entirely of carbon monoxide or of carbon monoxide containing only small amounts of other materials e.g. up to 10% v/v such as 1–10%, but the gas may if desired contain up to 95% v, e.g. 10–95% for example up to 60 % v e.g. 20–50% v based on the total volume of the gas), of other components such as nitrogen or argon which are inert. These gases may act as inert carrier gases. The gas comprising carbon monoxide is preferably substantially free from hydrogen. If it does contain some hydrogen, it is essential that the hydrogen content of the gas is less than 30, especially less than 20, preferably less than 10 and most preferably less than 5, % v based on the volume of carbon monoxide; the gas may contain 1–30% or 5–20% v/v hydrogen (based on carbon monoxide). The treatment may be carried out at any desired pressure e.g. 50–1000 kPa (0.5–10 bar) with, atmospheric pressure being preferred. The treatment time is not crucial, the optimum treatment time depending of course on the precise conditions such as the temperature and flow rate of the gas. Suitable treatment times are for example at least 10 minutes, preferably from 1 to 12 hours. The cobalt in the cobalt containing catalyst before said treatment is usually present at least partially in an oxidic form e.g. as free cobalt oxide or a mixed oxide with an oxidic support; the cobalt with catalyst before treatment may be in a major proportion in the oxide form with at most a minor proportion of cobalt metal; but especially, with a fresh catalyst may be substantially in the oxidic form. Under the preferred treatment conditions, the cobalt containing catalyst interacts with the carbon monoxide but avoids significant deposition, especially substantially any deposition of refractory carbon residues; thus conditions of 230°–270° C. for 10–1 hr at atmospheric pressure may be used, higher temperatures requiring shorter times. The interaction is believed to be a reduction of the oxidic cobalt catalyst; in particular to reduce the cobalt to give a product in which a majority of the cobalt is present as cobalt metal e.g. 51–99% such as 80–90% (as determined by hydrogen analysis or carbon dioxide analysis on the gaseous effluent from the treatment), and a minority of the cobalt is present as a cobalt oxide e.g. 1–49% such as 10–20%.

This treatment can be used as an activation for a fresh cobalt-containing catalyst, or it can be used as part of a regeneration sequence for a cobalt containing catalyst which has already been used in a Fischer-Tropsch reaction. In either case, the treatment leads to improved performance in a subsequent Fischer-Tropsch reaction. This improvement is not seen with conventional activation or regeneration treatments such as treatment at elevated temperature with hydrogen. Thus in a further embodiment, the present invention provides a method of increasing the activity and/or selectivity of a cobalt containing Fischer Tropsch catalyst towards $C_{5+}$ hydrocarbons, in which the catalyst has been treated by the process of the invention, and also provides the use of said treated catalyst for said purpose.

Prior to treatment with carbon monoxide, the cobalt-containing catalyst may be given a pre-treatment by treating at elevated temperature with a gas containing molecular oxygen, such as air. This pretreatment is especially useful with used Fischer Tropsch catalysts which can be oxidized by it to produce the cobalt containing catalyst in an oxidic form. The elevated temperature for this pre-treatment is usually in the range of from 200° to 600° C., especially 300° to 500° C. or 280°–550° C. The treatment may be carried out at any desired pressure, atmospheric pressure being preferred. The optimum treatment time will depend upon the history of the catalyst, on the oxygen content of the gas used and on the treatment conditions. The treatment time should in general be of sufficient length to remove any carbonaceous residues present on the catalyst especially one for regeneration. Treatment times of at least 30 minutes, preferably from 1 to 48 hours, are preferred.

A well known problem with Fischer-Tropsch reactions is the start-up procedure. To obtain stable conditions, a very long start-up period may be required. Temperature instabilities can lead to major difficulties. U.S. Pat. No. 4,626,552, describing these problems, states that it requires from 8 to 18 days to bring a Fischer-Tropsch reactor on stream, and discusses the problem of temperature runaway, caused by excessive heat and/or pressure during start-up. The present invention leads to a way of avoiding these problems. Thus, in a further embodiment, the present invention provides a process for the conversion of synthesis gas into hydrocarbons which comprises passing synthesis gas over a cobalt-containing catalyst under Fischer-Tropsch conditions; characterised in that the process comprises the following steps in succession: i) treating the cobalt-containing catalyst at elevated temperature with a gas containing carbon monoxide, said gas containing less than 30% v of hydrogen based on the volume of carbon monoxide; ii) passing synthesis gas over the cobalt-containing catalyst so treated at a temperature which is at least 10° C. higher than the maximum temperature attained during the subsequent step carried out under said Fischer-Tropsch conditions; and iii) passing synthesis gas over the cobalt-containing catalyst under said Fischer-Tropsch conditions. Benefits of step (ii) can be shortened start-up time to uniform Fischer Tropsch operation, a higher activity catalyst and better selectivity to $C_{5+}$ hydrocarbons.

Following the treatment step i) of the process according to the invention, the cobalt-containing catalyst is subjected to a start-up procedure, step ii), which involves passing synthesis gas over the cobalt-containing catalyst at a temperature which is at least 10° C. higher, preferably at least 20° C. higher such as 10°–150° C. especially 50°–110° C. higher than the maximum temperature attained during the subsequent Fischer-Tropsch reaction, step iii). Suitable temperatures for step (ii) are in the range of from 220° to 330° C. e.g. 230° to 300° C., especially 240° to 300° C. The pressure is preferably in the range of from 100 to 10,000 kPa (to 100 bar), more preferably 100 to 5,000 kPa (to 50 bar), especially 1,000 to 5,000 kPa (10 to 50 bar).

During step ii), it may be observed that an exotherm moves through the entire catalyst bed, especially with a fixed bed. The optimum period of time required for the step is that time required for the exotherm to move right through the bed. Once this has happened, it is desirable to end start-up step ii). The optimum duration of step ii) will depend on the flow ratio of carbon monoxide. Preferably the duration of step ii) is greater than 15 minutes, for example 0.5 to 12 hours.

The start-up step ii) is unusual in Fischer-Tropsch technology, where conventional wisdom is that high temperatures and pressures must be avoided during start-up in order to avoid temperature runaway and damage to the catalyst.

Following the start-up step ii), the desired Fischer-Tropsch reaction is carried out in step iii). Fischer-Tropsch conditions are well known to those skilled in the art. Preferably, the temperature is in the range of from 150° to 300° C., especially 180° to 240° C., most preferably 180° to 230° C. with a mean temperature of 190°–235° C. especially 195°–220° C., and the pressure is in the range of from 100 to 10,000 kPa (to 100 bar), more preferably 100 to 5000 kPa (to 50 bar), especially 1,000 to 5,000 kPa (10 to 50 bar). Preferably there is no interruption in the synthesis gas feed between steps ii) and iii), but if desired, the catalyst can be stored after step ii) is complete and used subsequently in step iii) when required. After step (ii), the temperature can be reduced to that required for the Fischer Tropsch process, but preferably the temperature is reduced to a temperature below 200° C. especially to 150°–190° C. before being raised again to the mean Fischer Tropsch operating temperature.

Synthesis gas is a mixture of hydrogen and carbon monoxide. The relative quantities of the two components may vary, but the molar ratio of hydrogen to carbon monoxide is usually in the range of from 1:1 to 3:1. Preferably the molar ratio of hydrogen to carbon monoxide is in the range of from 1.8:1 to 2.2:1. The feedstock gas used in step ii) or step iii) may if desired contain other components, for example nitrogen, paraffins, olefins and/or carbon dioxide. Nitrogen may be present to act as a carrier gas or co-feed, and if so is preferably present in an amount of less than 40% v, for example from 10 to 40% v. Other components are preferably present in minor amounts, typically less than 20%, especially less than 15, % v.

The cobalt catalyst used in the present invention preferably comprises cobalt on a support. Very many suitable supports may be used, for example silica, alumina, titania, ceria, zirconia or zinc oxide. The support may itself have some catalytic activity. Preferably the catalyst contains from 2 to 35% w, especially from 5 to 25% w, of cobalt. Alternatively, the cobalt catalyst may be used without a support. In this case, the catalyst is often prepared in the form of cobalt oxide. Active metal catalytic components or promoters may be present as well as cobalt if desired.

The process of the invention may be performed in a fluid bed or a fixed bed or in a slurry in a liquid e.g. of liquid hydrocarbon product. The treatment process of the invention with carbon monoxide e.g. step (i) above may be performed in the same or a different reactor from that of the start-up or Fischer Tropsch step (e.g. (ii) or (iii) above).

The following Examples 1 and 3–5 illustrate the invention.

EXAMPLE 1

Catalyst Preparation

A catalyst containing 10% wt cobalt on zinc oxide was prepared as follows.

Deionised water (3.35 kg) was added to ZnO (10.00 kg) with mixing. After 5 minutes $Co(NO_3)_2.6H_2O$ (5.55 kg) dissolved in deionised water (4.15 kg) was added with stirring using a Z-blade mixer. After mixing the water was removed by drying in air at 120° C. for 15 hours to leave a product, which was then further heated to 500° C. (at a rate of 50° C./h) and then maintained at 500° C. for a further 5 hours. The calcined catalyst obtained (9.23 kg) was lubricated with 2 wt % stearic acid and formed into tablets 3.175 mm (⅛" diameter×2 mm) which were subsequently heated to 500° C. (at a rate of 100° C./h) and then maintained at 500° C. for 1 hour in air. The tablets were cooled to room temperature in air, ground and sieved to 250–500 μm mesh size.

EXAMPLE 2 (COMPARATIVE)

In situ $H_2$ Pretreatment 10 g (250–500 μm) of the catalyst prepared in Example 1 were charged into a microreactor. Hydrogen was introduced at a GHSV (gas hourly space velocity) of 1000 $h^{-1}$ and the temperature raised from 30° C. to 320° C. at 10° C. $min^{-1}$. The temperature was held at 320° C. for 10 h, and then the reactor cooled at 10° C. $min^{-1}$ to room temperature.

EXAMPLE 3

3 h Carbon Monoxide in situ Reduction 10 g (250–500 μm) of the catalyst prepared in Example 1 were charged into a microreactor. Nitrogen was introduced at GHSV=1000 $h^{-1}$ and the temperature raised from 30° C. to 250° C. at 10° C. $min^{-1}$. Then the nitrogen was switched off and carbon monoxide introduced at GHSV-900 $h^{-1}$ for 3 h. The reactor was then cooled at 10° C. $min^{-1}$ to 30° C.

EXAMPLE 4

In situ Air Pretreatment Followed by 3 h Carbon Monoxide Reduction 10 g (250–500 μm) of the catalyst prepared in Example 1 were charged into a microreactor. Air was introduced at GHSV=6000 $h^{-1}$ and the temperature raised from 30° to 500° C. at 10° C. $min^{-1}$. The temperature was held at 500° C. for 44 h and then cooled to 250° C. Carbon monoxide was introduced at GHSV=900 $h^{-1}$ and after 3 h at 250° C. the reactor was cooled at 10° C. $min^{-1}$ to 30° C.

Catalysts from Examples 2, 3 and 4 were all tested using the following procedure.

Reaction Start-up and Fischer-Tropsch Reaction

Following on from Examples 2, 3 and 4 the microreactor at a temperature below 30° C., was purged with a gas mixture containing 20% v nitrogen, and also hydrogen and carbon monoxide in a molar ratio of 2.07:1. The pressure was then increased to 3000 KPa (30 bar) and the GHSV of the gas mixture passed adjusted to 1250 h$^{-1}$. The applied temperature was raised to 250° C. at 2° C. min$^{-1}$, and then held for 1 h at 250° C. The bed temperature was then decreased to 180° C. and then slowly increased until about 80% carbon monoxide conversion was achieved. Conversion was measured from gas chromatography analysis of exit gas using N$_2$ marker. The results are shown in Tables 1 to 4. Productivity C$_{5+}$ is the total number of grams of C$_{5+}$ product formed per liter of catalyst per hour.

Because the tests were arranged to run at constant conversion, the bed temperature observed gives a measure of the activity of the catalyst being tested. Thus, a more active catalyst can achieve an 80% carbon monoxide conversion at a lower temperature than a less active catalyst.

Comparison of Tables 1 and 2 shows that the catalyst treated with carbon monoxide according to the invention shows higher initial activity than the catalyst given a conventional hydrogen treatment. In addition, production of undesired C$_1$ products is considerably lower and production of the desired C$_{5+}$ products is considerably higher.

Table 3 shows the additional benefits of an air treatment followed by a carbon monoxide treatment: the productivity is considerably increased.

EXAMPLE 5

A 10% cobalt on zinc oxide catalyst was prepared by the general method of Example 1. One portion of the catalyst was treated with air for 6 hours at 500° C. followed by hydrogen for 9 hours at 320° C., while a second portion was treated with air for 50 hours at 500° C. followed by carbon monoxide for 3 hours at 250° C. Both catalysts were then tested by the method described above. The results are given in Table 4 below, and show the clear advantages of the treatment involving carbon monoxide.

TABLE 4

| Catalyst Treatment | Hours on Stream | Mean Bed Temp (°C.) | CO Conversion (%) | % Carbon Molar Selectivity | | |
|---|---|---|---|---|---|---|
| | | | | CH$_4$ | CO$_2$ | C$_{5+}$ |
| Air/H$_2$ (Comparative) | 214 | 214 | 87 | 7.5 | 2.5 | 76.8 |
| Air/CO | 213 | 212 | 87 | 4.6 | 1.9 | 91.0 |

EXAMPLE 6

An Unsupported Catalyst

Preparation

Ammonium bicarbonate (1145 g) was dissolved in deionised water (10.4 dm$^3$) and 500 cm$^3$ of the solution added to a continuous precipitation cup. In a second vessel cobaltous

TABLE 1

Catalyst Treatment According to Example 2 (Comparative)

| Hours on Stream | Mean Bed Temp (°C.) | Conversion | | % Carbon Molar Selectivity | | | | | | Bed Prod |
|---|---|---|---|---|---|---|---|---|---|---|
| | | CO | H$_2$ | CH$_4$ | CO$_2$ | C$_2$ | C$_{2+}$C$_4$ | C$_{5+}$ | C$_{2+}$ | C$_{5+}$ |
| 54 | 214 | 73.9 | 82.8 | 8.0 | 0.5 | 1.7 | 9.0 | 80.9 | 91.5 | 125 |
| 149 | 216 | 74.2 | 80.1 | 7.8 | 1.4 | 1.3 | 6.9 | 82.6 | 90.8 | 128 |

TABLE 2

Catalyst Treated According to Example 3

| Hours on Stream | Mean Bed Temp (°C.) | Conversion | | % Carbon Molar Selectivity | | | | | | Productivity |
|---|---|---|---|---|---|---|---|---|---|---|
| | | CO | H$_2$ | CH$_4$ | CO$_2$ | C$_2$ | C$_{2+}$C$_4$ | C$_{5+}$ | C$_{2+}$ | C$_{5+}$ |
| 26 | 204 | 78.7 | 82.2 | 5.9 | 1.1 | 0.6 | 3.6 | 88.8 | 93.0 | 145 |
| 77 | 209 | 83.9 | 90.4 | 7.1 | 2.4 | 0.5 | 2.2 | 87.8 | 90.6 | 153 |
| 149 | 210 | 86.4 | 88.5 | 7.0 | 2.2 | 0.5 | 2.2 | 88.0 | 90.8 | 158 |

TABLE 3

Catalyst Treated According to Example 4

| Hours on Stream | Mean Bed Temp (°C.) | Conversion | | % Carbon Molar Selectivity | | | | | | Productivity |
|---|---|---|---|---|---|---|---|---|---|---|
| | | CO | H$_2$ | CH$_4$ | CO$_2$ | C$_2$ | C$_{2+}$C$_4$ | C$_{5+}$ | C$_{2+}$ | C$_{5+}$ |
| 26 | 204 | 90.4 | 92.5 | 7.6 | 1.5 | 0.7 | 3.4 | 86.8 | 90.9 | 163 |
| 94 | 205 | 84.2 | 87.1 | 5.5 | 0.8 | 0.5 | 2.6 | 90.6 | 93.7 | 159 |
| 144 | 205 | 79.8 | 80.6 | 6.2 | 0.8 | 0.6 | 3.4 | 89.0 | 93.0 | 148 | nitrate (450.6 g) was dissolved in deionised water (2.8 dm$^3$). The two solutions were pumped simultaneously into the solution already in the precipitation cup at such a rate as to ensure complete precipitation of cobalt oxide (rapid agitation was required within the precipitation cup). The precipitate was constantly being removed via a weir and filtered on a Buchner funnel. The complete precipitation process was completed in 2 hours. The filter cake was dried overnight in air at 150° C. and then in air at 350° C. for 6 hr to give 114.4 g of $Co_3O_4$.

Test

A portion of the above catalyst was treated with hydrogen as described in Example 2 and tested using the reaction start-up procedure described earlier. The results are shown in the first row of Table 5. The catalyst so tested was then treated with 1% $O_2$/99% $N_2$ at 500° C. for 23 hours. The temperature was then reduced to 250° C. and the catalyst treated with CO for 3 hours. The catalyst was again tested using the same reaction start-up procedure. The much improved results are shown in the second row of Table 5.

TABLE 5

| Catalyst Treatment | Hours on Stream | Mean Bed Temp (°C.) | CO Conversion (%) | % Carbon Molar Selectivity | | |
|---|---|---|---|---|---|---|
| | | | | $CH_4$ | $CO_2$ | $C_{5+}$ |
| $H_2$ (Comparative) | 25 | 257 | 33 | 37.4 | 1.3 | 28 |
| 1% $O_2$/CO | 25 | 231 | 69 | 14.1 | 1.5 | 105 |

We claim:

1. A process for reducing a catalyst containing cobalt, suitable for use in a Fischer Tropsch process for converting synthesis gas into hydrocarbons, which comprises pretreating said cobalt catalyst at 200°–600° C. with a gas containing molecular oxygen to produce an oxidized cobalt catalyst, a majority of said cobalt being in an oxide form, and then contacting said oxidized cobalt catalyst at elevated temperature with a gas containing carbon monoxide substantially free of hydrogen, to produce a reduced cobalt containing catalyst.

2. A process according to claim 1 wherein said oxide containing catalyst comprises cobalt on a support.

3. A process according to claim 1 wherein the catalyst is contacted with a gas comprised substantially entirely of carbon monoxide.

4. A process according to claim 1 wherein the gas contacts the catalyst at 230°–260° C.

5. A process according to claim 1 further comprising prior to contacting said catalyst with said carbon monoxide contacting a catalyst containing cobalt at 380°–600° C., with a gas containing molecular oxygen to obtain said catalyst having at least a majority of said cobalt in an oxide form.

6. A process for reducing a catalyst which comprises pretreating a cobalt catalyst on a support at 200°–600° C. with a gas containing molecular oxygen to produce an oxidized cobalt catalyst at least some of which is in an oxide form, and then contacting said oxidized cobalt catalyst at an elevated temperature in the range of 200° C. to 250° C. with a gas containing carbon monoxide substantially free of hydrogen to produce a reduced cobalt containing catalyst.

7. A process for reducing a catalyst at least some of which is in an oxide form comprising contacting a cobalt catalyst on a support at an elevated temperature in the range of 380° C. to 600° C. with a gas containing molecular oxygen and then reducing the product obtained at 200°–350° C. with a gas containing carbon monoxide substantially free of hydrogen, to produce a reduced cobalt containing catalyst.

8. The process according to claim 7 which is followed by passing synthesis gas over the treated cobalt containing catalyst under Fischer Tropsch conditions to form hydrocarbons.

9. A process according to claim 6 wherein the gas contacts the catalyst at 230° C. to 260° C.

10. A process according to claim 1 wherein said catalyst contains cobalt substantially in oxide form.

11. A process according to claim 1 wherein said reduced cobalt containing catalyst is comprised of a majority of cobalt metal.

12. A process according to claim 6 wherein said catalyst contains cobalt substantially in oxide form.

13. A process according to claim 6 wherein said reduced cobalt containing catalyst is comprised of a majority of cobalt metal.

14. A process according to claim 1, wherein said cobalt catalyst which is pretreated by oxidation is a cobalt catalyst which has already been used in a Fischer Tropsch reaction.

15. A process according to claim 6, wherein said cobalt catalyst which is pretreated by oxidation is a cobalt catalyst which has already been used in a Fischer Tropsch reaction.

16. A process according to claim 14 which further comprises cooling the oxidized cobalt catalyst to 230°–260° C. before contacting with carbon monoxide at 230°–260° C.

17. A process according to claim 15 which further comprises cooling the oxidized cobalt catalyst to 230°–260° C. before contacting with carbon monoxide at 230°–260° C.

* * * * *